United States Patent [19]

Schmidt

[11] 4,284,782

[45] Aug. 18, 1981

[54] PROCESS FOR THE MANUFACTURE OF 6-HYDROXYPYRID-2-ONES

[75] Inventor: Frank Schmidt, Bruchköbel, Fed. Rep. of Germany

[73] Assignee: Cassella Aktiengesellschaft, Frankfurt, Fed. Rep. of Germany

[21] Appl. No.: 76,237

[22] Filed: Sep. 17, 1979

[30] Foreign Application Priority Data

Oct. 21, 1978 [DE] Fed. Rep. of Germany ....... 2845863

[51] Int. Cl.³ ......................................... C07D 239/22
[52] U.S. Cl. ................................................. 546/288
[58] Field of Search ........................................ 546/288

[56] References Cited

U.S. PATENT DOCUMENTS 4,083,849  4/1978  Quadbeck-Seeger ................ 546/288

FOREIGN PATENT DOCUMENTS 2307445  2/1973  Fed. Rep. of Germany .......... 546/288
2330681  3/1977  France ................................... 546/288

OTHER PUBLICATIONS

Berichte der Deutschen Chemischen Gesellschaft, 26/IV, (1897), pp. 654–656.

Primary Examiner—Henry R. Jiles
Assistant Examiner—Robert C. Whittenbaugh
Attorney, Agent, or Firm—Connolly and Hutz

[57] ABSTRACT

The manufacture of 6-hydroxypyrid-2-ones is achieved by reacting a cyanoacetamide with an acetoacetic acid ester at temperatures of 50° to 200° C. and a pressure of 0.5 to 50 bars in an aqueous solution or suspension in the presence of an amine in a molar amount at least equal to that of the cyanoacetamide reactant.

8 Claims, No Drawings

PROCESS FOR THE MANUFACTURE OF 6-HYDROXYPYRID-2-ONES

The present invention relates to a process for the manufacture of 6-hydroxypyrid-2-ones of the general formula I

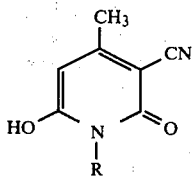

wherein R represents hydrogen or an optionally branched alkyl radical having 1 to 4 carbon atoms, by reacting cyanoacetamides with acetoacetic acid esters, in which process cyanoacetamides of the formula II

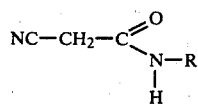

wherein R has the abovementioned meaning, or a mixture of substances containing essentially cyanoacetamides of the formula II, are warmed at temperatures between 50° and 200° C. in aqueous solution or suspension under a pressure of 0.5 to 50 bars, with acetoacetic acid esters of the formula III

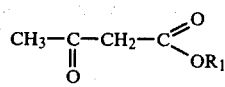

wherein $R_1$ designates an aliphatic radical having 1 to 8 carbon atoms or a cycloaliphatic radical having 3 to 6 carbon atoms, in the presence of at least one mol of an amine of formula IV

wherein R has the abovementioned meaning.

6-Hydroxypyrid-2-ones (formula I, R=hydrogen) which are unsubstituted at the pyridone nitrogen have been known for a long time. They were first discovered and described by Guareschi in the reaction of β-ketocarboxylic acid esters with cyanoacetamide (Mem. Accad. Torino cl. sci. fis. mat. e nat. [2], volume 46, page 11; Chemisches Zentralblatt 1896 I, 601). Other authors have obtained this compound by cyclising the reaction product of acetoacetic acid ethyl ester with malodinitrile (for example Kasturi, T.R.; Sharma, V.K.; Srinivasan, A.; Subrahmanyam, G.; Tetrahedron 29 (1973) 24, 4,103–09 and Gudriniece, E.; Rigerte, B.; Latv. PSR Zinat. Akad. Vestis, Kim. Ser. (1974) (2), (239–40). A process for the preparation of 5-cyanopyrid-6-ones by reacting halogenoacetic acid esters with nitrogen compounds and subsequently reacting the reaction mixture with alkali metal cyanides and then with dicarbonyl compounds is described in German Document No. 2,531,035 open for Inspection. This process constitutes a modification of the known Guareschi process - the reaction of cyanoacetamide with acetoacetic ester - in which, however, there is put in as an initial stage the preparation of the cyanoacetamide from chloroacetic acid by esterifying the latter, ammonolysing the ester to give chloroacetamide and reacting this product with sodium cyanide to give cyanoacetamide. Subjecting acetoacetic acid ethyl ester and cyanoacetamide to a condensation reaction in the presence of piperidine or potassium hydroxide to give 3-cyano-2,6-dihydroxy-4-methylpyridine, in order to improve the yield of the valuable end product, has also already been described (Journal of Organic Chemistry, volume 25 (1960), pages 560–564). Finally, a process for the preparation of N-alkylsubstituted 6-hydroxypyrid-2-ones, in which the cyanoacetic acid ethyl ester, acetoacetic acid ethyl ester and an alkylamine are reacted in alkanoic solution at 110° to 120° C. in an autoclave is known from German Document No. 1,956,142 open for inspection. In this case the amine is employed in a pure form and, after the completion of the reaction, the alkanol used as the solvent must be removed by distillation. If, for example, 1,4-dimethyl-3-cyano-6-hydroxypyrid-2-one is prepared by the instructions of this publication by reacting 1 mol of cyanoacetic acid ethyl ester, 1 mol of acetoacetic acid ethyl ester, 2 mols of methylamine and approx. 700 ml of n-butanol as solvent at a temperature of 115° C., a yield of about 70% is obtained after a reaction time of 4 hours, approx. 79% after a reaction time of 8 hours and approx. 80% after a reaction time of 16 hours. It is found in this connection that this known process evidently tends towards a limiting yield value at about 80% of theory, which is not exceeded even with a considerably prolonged reaction time. Apart from the fact that reaction times of 8 or 16 hours lead to a very poor space-time yield for the process, 80% of theory is also unsatisfactory for an industrial process, since not only must a loss of end product be accepted, but also the 20% of starting materials and by-products have to be eliminated in an ecologically satisfactory manner, which causes additional costs.

In view of the high value of the compounds of the formula I, a manufacturing process giving a high yields as possible was, therefore, urgently desired.

It was now been found, surprisingly, that 6-hydroxypyrid-2-ones of the general formula I are obtained in substantially improved yields and in very good purity if cyanoacetamides of the formula II or a mixture of substances containing essentially cyanoacetamides of the formula II are warmed at temperatures between 50° and 200° C. in aqueous solution or suspension under a pressure of 0.5 to 50 bars with acetoacetic acid esters of the formula III in the presence of at least one mol of an amine of the formula IV.

In this context, R in the formulae I, II and IV represents hydrogen or an optionally branched alkyl radical having 1 to 4 carbon atoms. Alkyl radicals of this type, having 1 to 4 carbon atoms and represented by R are methyl, ethyl, 1-propyl, 2-propyl, 1-butyl, 2-butyl, 2-methylprop-1-yl and 2-methylprop-2-yl. R is preferably hydrogen, methyl or ethyl.

An essential characteristic of the process according to the invention is the presence of water. The quantity of water used is at least 10 percent by weight relative to the weight of the cyanoacetamide employed. As a rule, 10 to 1,000 percent by weight, preferably 50 to 500 percent by weight, of water are employed, for economic reasons.

In the cyanoacetamides of the formula II which are employed for the process according to the invention, R has in each case the same meaning as in the 6-hydroxypyrid-2-one to be prepared.

The cyanoacetamides of the formula II which are used as starting materials are known compounds and can be prepared in a simple manner by processes known from the literature (for example B. B. Corson, R. W. Scott & C. E. Vose, Organic Syntheses, Coll. Vol. I, 179 (1941); H. Henecka & P. Kurtz, Houben-Weyl, Methoden der Organischen Chemie (Methods of Organic Chemistry), volume 8, page 658 (1952)). In accordance with these known processes, the cyanoacetamides of the formula II can be obtained by reacting cyanoacetic acid esters with amines of the formula $NH_2$-R with the elimination of alcohols.

In the acetoacetic esters of the formula III which are used as the starting material for the process according to the invention, $R_1$ denotes an aliphatic radical having 1 to 8 carbon atoms or a cycloaliphatic radical having 3 to 6 carbon atoms. These radicals can, in principle, be saturated or unsaturated, or branched or unbranched. The use of acetoacetic esters in which $R_1$ is unsaturated can, however, lead to complications, because unsaturated compounds of this type tend to polymerise and side-reactions cannot, therefore, be excluded. The use of acetoacetic esters which are unsaturated in the alcohol radical is, therefore, avoided as a rule. The acetoacetic esters of the formula III which are normally employed are those in which $R_1$ denotes an alkyl radical having 1 to 8 carbon atoms or a cycloalkyl radical having 3 to 6, preferably 5 or 6, carbon atoms. For reasons of technical accessibility, it is preferable to employ acetoacetic esters of the formula III in which $R_1$ denotes a lower alkyl radical having 1 to 4 carbon atoms, especially a methyl or ethyl radical.

In carrying out the process according to the invention, 1.0 to 1.5 mols, preferably 1.0 to 1.3 mols, of acetoacetic acid ester of the formula III are employed, relative to 1 mol of cyanoacetamide of the formula II.

According to the meaning of R in the 6-hydroxypyrid-2-one to be prepared, amines of the formula IV in which R denotes hydrogen or an optionally branched alkyl group having 1 to 4 carbon atoms, are employed. Amines of this type are monomethylamine, monoethylamine, monopropylamine, monoisopropylamine, monobut-1-ylamine, monobut-2-ylamine, monoisobutylamine or monotert.-butylamine. The said amines can be employed in a pure form or, to the extent that they are water-soluble, also in the form of their concentrated aqueous solutions. Since aqueous solutions are as a rule initially produced in the manufacture of ammonia or lower alkylamines, the use of such solutions for carrying out the process according to the invention is particularly advantageous and preferred.

If the reaction according to the invention is carried out using anhydrous amines of the formula IV, the necessary quantity of water mentioned above must be added separately to the reaction mixture. With the preferred use of aqueous amine solutions the separate addition of water can be reduced or completely omitted, depending of the quantity of water introduced with the amine solution. The aqueous amine solutions can contain 5 to 80, preferably 20 to 50, percent by weight of the amine to be employed.

At least 1 mol of the amine of the formula IV must be employed per mol of cyanoacetamide of the formula II employed. There is no upper limit to the quantity of the amine. On economic considerations, however, 1.0 to 2 mols, preferably 1.0 to 1.15 mols, of amine are used.

It is a particular advantage of the process according to the invention that it is not absolutely necessary to use in a pure form the cyanoacetamides employed as the starting material, but that they can equally well be in the form of a mixture with other chemical substances, provided that the latter are inert towards the reactants of the process. Such mixtures should contain cyanoacetamides of the formula II essentially, that is to say more than 50 percent by weight. Mixtures of this type, containing essentially cyanoacetamides of the formula II, which can be employed in the process according to the invention are in particular those which are obtained as crude reaction mixtures in the reaction of cyanoacetic esters with amines of the formula IV. In addition to the necessary cyanoacetamide of the formula II, these reaction mixtures also contain an excess of amines of the formula IV, the aliphatic hydroxy compound $R_1OH$ formed in the reaction of the cyanoacetic ester with the amine and, possibly, small quantities of by-products.

The use of such crude reaction mixtures, containing essentially cyanoacetamides of the formula II, instead of the pure compounds, affords the advantage that the entire effort required to isolate and purify these cyanoacetamides can be avoided, and, in addition, the process starts from materials which are cheaper because they are simpler to prepare, namely the cyanoacetic acid esters. Since the use of these crude reaction mixtures additionally entails no reduction, or virtually no reduction, in the yield of 6-hydroxypyrid-2-ones of the formula I, it is preferable to carry out the process according to the invention using the crude reaction mixtures containing essentially cyanoacetamides of the formula II.

In order to carry out the process according to the invention, the reactants are mixed in the ratios indicated above and the mixture is warmed in a pressure-resistant, closed vessel to a temperature between 50° and 200° C., preferably between 80° and 120° C. The reaction can be carried out at 0.5 to 50 bars under the pressure of an inert extraneous gas. It is preferable to carry out the reaction under the autogenous pressure of the reaction system at the reaction temperature selected. Depending on the reactants and the reaction temperature selected, this autogenous pressure can be between 0.5 and 50 bars. In the preferred temperature range, a pressure of 1 to 15 bars is reached. In order to maintain a uniform distribution of material in the reaction mixture, especially when the reaction is carried out in suspension, it is appropriate to ensure continuous thorough mixing of the batch, for example by stirring.

If it is intended to carry out the process according to the invention using crude reaction mixtures containing essentially cyanoacetamides of the formula II, a cyanoacetic acid ester of the formula V

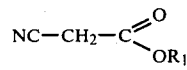

(V)

wherein $R_1$ has the abovementioned meaning is reacted with at least 1 mol, preferably 1 to 1.15 mols, relative to 1 mol of the ester, of an amine of the formula IV, especially in the form of a 5 to 80 percent strength by weight, preferably 20 to 50 percent strength by weight, aqueous solution, temperatures between 0° and 100° C., preferably 5° to 80° C., being used.

During the reaction it is advantageous to ensure good mixing, for example by stirring. Depending on the reactivity of the esters of the formula V and amines of the formula IV employed and on the reaction temperature selected, the reaction time until virtually complete conversion is achieved is 1 to approx. 12 hours. Thus, for example, the reaction of cyanoacetic acid ethyl ester with a 40% strength aqueous solution of methylamine at 5° to 10° C. is one hour, while the corresponding reaction with a 50% strength solution of n-butylamine at 20° to 30° C. is 12 hours or 3 hours at 60° to 80° C. The progress of the reaction can be followed by thin layer chromatography.

After the formation of the cyanoacetic acid amide has been completed, a further addition of at least 1 mol, preferably 1 to 1.15 mols, of the same amine is made to the reaction mixture at a temperature between 0° and 30° C. 1 to 1.5 mols, preferably 1 to 1.3 mols, of an acetoacetic acid ester of the formula III, preferably acetoacetic acid methyl or ethyl ester, are then added to the batch, per mol of cyanoacetic ester employed, also at temperatures between 0° and 30° C., if necessary with cooling.

It is also possible to charge initially the whole quantity of amine of at least 2 mols, preferably 2 to 2.3 mols, since this is not only technically simpler, but is also more advantageous for the kinetics of the reaction with the cyanoacetic ester. When all the reactants have been combined in the manner indicated, the reaction mixture is raised to a temperature between 50° and 200° C. as described above, in a pressure-resistant, closed vessel, and is kept at this temperature, appropriately while stirring, until the reaction to give the desired 6-hydroxypyrid-2-one is complete. The reaction time is usually between two and six hours.

The isolation of the 6-hydroxypyrid-2-ones is effected—if appropriate after diluting the reaction solution or suspension with water—by acidifying with mineral acids, preferably hydrochloric acid or sulphuric acid, at temperatures between 0° and 100° C., preferably 20° and 70° C., if appropriate cooling the mixture to 0° to 30° C. and subsequently filtering off the precipitated product.

If it is desired to recover the amine combined in the form of the corresponding ammonium salt of the particular 6-hydroxypyrid-2-one and also the amine which may have been used in excess, 2.0 to 5.0 mols of alkali metal hydroxide, optionally in the form of an aqueous solution, are added to the reaction mixture after the pressure reaction is complete and 1.0 to 2.0 mols of amine are then distilled off, appropriately into a receiver charged with water, so that an aqueous amine solution which can be used for further batches is formed immediately.

The 6-hydroxypyrid-2-one can then be isolated from the aqueous distillation residue, as indicated above, by acidifying, optionally cooling and filtering off. Compared with the nearest comparable process of German Document No. 1,956,142, open for inspection the process according to the invention leads to a substantial increase in the yield, for example in the case of the preparation of 1,4-dimethyl-3-cyano-6-hydroxypyrid-2-one, to an increase in the yield of approx. 12 to 15% of theory. Associated with this increase in the yield there is a decline considerably exceeding 50% in the by-products which have to be removed. The process according to the invention is carried out with shorter reaction times and higher concentrations and therefore gives considerably better space-time yields than the known processes. Since the process according to the invention is carried out in an aqueous medium, the recovery of organic solvents is eliminated, such as, for example, the recovery of n-butanol by steam distillation such as is necessary in the nearest comparable known process. At the same time as the recovery of organic solvents is eliminated, there is also the advantage of decreased environmental pollution, since, in the process according to the invention, it is also not possible for losses of solvent, which are otherwise unavoidable, to occur. The fact that it is possible to employ aqueous solutions of amines is also advantageous from a technical point of view, especially since the recovery of the excess quantities of amine produces, in turn, aqueous solutions which can be recycled immediately into the process, thus producing neither pollution of the environment nor a particular effort for the regular removal of waste material.

With regard to the state of the art, it was extremely surprising and not to be foreseen, that the reactions of the process according to the invention take place readily and almost completely in the presence of water. The opposite would have been expected on the basis of theory, since the reactions mentioned could be adversely affected in the presence of water as a result of side-reactions taking place. It was a further surprising observation that the process according to the invention can also be carried out without complications when crude cyanoacetamide mixtures are employed.

The illustrative embodiments which follow illustrate the execution of the process according to the invention. "Parts" are parts by weight and percentages are percentages by weight.

EXAMPLE 1

250 parts of water, 98 parts of N-methylcyanoacetamide and 169 parts of acetoacetic acid ethyl ester are initially placed in an autoclave, 40 parts of gaseous monomethylamine are injected, while stirring, and the reaction mixture is then heated at 90° C. for 3 hours, a pressure of 2.9 bars being generated. The batch is diluted with 400 parts of water, 80 parts of 61% strength sulphuric acid are added at 30°–35° C., the batch is cooled to 20° C. and the precipitate which has been formed is filtered off. 155.8 parts (95% of theory) of 1,4-dimethyl-3-cyano-6-hydroxypyrid-2-one with a melting point of 285° C. are obtained.

Similar results are obtained if the reaction is carried out under nitrogen pressure of 10 or 20 bars.

Comparable results are also obtained if equivalent quantities of N-ethylcyanoacetamide or N-isopropylcyanoacetamide and ethylamine or isopropylamine are employed instead of N-methylcyanoacetamide and monomethylamine, respectively.

EXAMPLE 2

99 parts of cyanoacetic acid methyl ester are added at 5°–10° C., while stirring, to 162 parts of a 44.1% strength aqueous solution of monomethylamine, stirring is continued for one hour, 133.5 parts of acetoacetic acid methyl ester are run in and the mixture is heated at 90° C. for 4 hours in an autoclave, a maximum pressure of 1.3 bars being generated. 296 parts of 27% strength sodium hydroxide solution are then added to the reaction solution and 33 parts of monomethylamine (46.2% of theory, relative to material employed) are distilled, at 85° C., into a receiver charged with approx. 42 parts of ice water, so that an approx. 44% strength aqueous solution of monomethylamine, suitable for further reactions is formed. The 1,4-dimethyl-3-cyano-6-hydroxypyrid-2-one is then precipitated by being run into a mixture of 100 parts of ice and 217 parts of 61% strength sulphuric acid. The product is filtered off, washed with water and dried.

Yield: 155.8 parts (95% of theory) with a melting point of 285° C.

If the equivalent quantity of cyanoacetic acid butyl or isooctyl ester is employed instead of the cyanoacetic acid methyl ester, similar results are obtained.

EXAMPLE 3

3-cyano-4-methyl-6-hydroxypyrid-2-one is prepared by running 99 parts of cyanoacetic acid methyl ester into 160 parts of 24% strength aqueous ammonia, while stirring, at 10° to 15° C. The mixture is stirred for approx. 1 hour at 20° C., 133.5 parts of acetoacetic acid methyl ester are then added and the reaction mixture is heated at 80° C. for 4 hours in an autoclave, a maximum pressure of 1.5 bars being generated. The reaction suspension is then diluted with 400 parts of water and 114 parts of 61% strength sulphuric acid are added at 50°-60° C. and the mixture is cooled to 20° C. The product precipitated is filtered off, washed with water and dried. This gives 147.0 parts (98% of theory) of 3-cyano-4-methyl-6-hydroxypyrid-2-one with a melting point above 305° C.

If a 5% or 15% or 20% strength aqueous ammonia solution is used instead of the 24% strength aqueous ammonia, similar results are obtained.

EXAMPLE 4

99 parts of cyanoacetic acid methyl ester are added at 5°-15° C. to 184.4 parts of a 49.4% strength aqueous solution of ethylamine, while stirring, stirring is continued for one hour, 133.5 parts of acetoacetic acid methyl ester are added and the mixture is heated at 100° C. for 5 hours in an autoclave, a pressure of 10.5 bars being generated. The reaction solution is then diluted with 600 parts of water and acidified with 74 parts of 61% strength sulphuric acid. The precipitated product is filtered off, washed and dried. This gives 153 parts (85.9% of theory) of 1-ethyl-3-cyano-4-methyl-6-hydroxypyrid-2-one with a melting point of 242°-45° C.

If the equivalent quantity of acetoacetic acid propyl or cyclohexyl ester is used instead of the acetoacetic acid methyl ester, similar results are obtained.

EXAMPLE 5

69.3 parts of cyanoacetic acid methyl ester are added at 20° to 30° C. to 117.5 parts of n-butylamine, while stirring, the mixture is stirred for approx. 12 hours, 150 parts of water and 93.4 parts of acetoacetic acid methyl ester are added and the mixture is heated at 120° C. for 6 hours in an autoclave, a pressure of 13 bars being generated. The reaction solution is then run into a mixture of 400 parts of water and 75 parts of 61% strength sulphuric acid and the precipitate which has been formed is filtered off, rinsed with water and dried, 123 parts (85% of theory) of 1-butyl-3-cyano-4-methyl-6-hydroxypyrid-2-one with a melting point of 220° C. are obtained.

If n-propylamine or isopropylamine—optionally in the form of a 5-80% strength aqueous solution—are employed instead of n-butylamine analogously to the above example, the corresponding 1-propyl-3-cyano-6-hydroxypyrid-2-one or 1-isopropyl-3-cyano-6-hydroxypyrid-2-one with a melting point of 239°-240° C. or 252° C., respectively, is isolated.

We claim:

1. In the process for the manufacture of 6-hydroxypyrid-2-ones of the formula

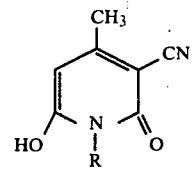

wherein R is hydrogen or alkyl having 1 to 4 carbon atoms comprising reacting a cyanoacetamide of the formula

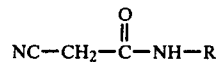

with an acetoacetic acid ester of the formula

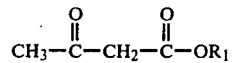

wherein $R_1$ is selected from the group consisting of alkyl having 1 to 8 carbon atoms, alkenyl having 1 to 8 carbon atoms, cycloalkyl having 3 to 6 carbon atoms and cycloalkenyl having 3 to 6 carbon atoms, at elevated temperatures in an aqueous solution or suspension in the presence of a basic compound in a molar amount at least equal to that of said cyanoacetamide, the improvement comprises said basic compound being an amine of the formula $RNH_2$ with R being the identical to the pyridone nitrogen substituent, and the reaction is carried out at temperatures from 50° to 200° C. at superatmospheric pressure of 0.5 to 50 bars.

2. The process according to claim 1, wherein $R_1$ is selected from the group consisting of alkyl having 1 to 8 carbon atoms and cycloalkyl having 3 to 6 carbon atoms.

3. The process according to claim 1, wherein $R_1$ is selected from the group consisting of alkyl having 1 to 8 carbon atoms and cycloalkyl having 5 to 6 carbon atoms.

4. The process according to claim 1, wherein $R_1$ is alkyl having 1 to 4 carbon atoms.

5. The process according to claim 1, wherein the cyanoacetamide is the crude reaction product obtained by reacting a cyanoacetic acid ester of the formula

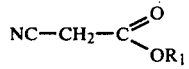

with an amine of the formula $RNH_2$.

6. The process according to claim 1 wherein the reaction pressure is the total of the partial pressures of the constituents of the reaction mixture at the reaction temperature.

7. The process according to claim 1, wherein the reaction temperature is between 80° and 120° C.

8. The process according to claim 1, wherein R is hydrogen, methyl or ethyl.

* * * * *